United States Patent
Rao

(10) Patent No.: US 8,827,137 B2
(45) Date of Patent: Sep. 9, 2014

(54) PIN ALIGNMENT ASSEMBLY FOR SURGICAL STAPLER

(75) Inventor: Ramesh Srinivasa Rao, Karnataka (IN)

(73) Assignee: Covidien LP, Mansfield, MA (US)

( * ) Notice: Subject to any disclaimer, the term of this patent is extended or adjusted under 35 U.S.C. 154(b) by 367 days.

(21) Appl. No.: 13/028,608

(22) Filed: Feb. 16, 2011

(65) Prior Publication Data

US 2011/0233261 A1     Sep. 29, 2011

Related U.S. Application Data

(60) Provisional application No. 61/317,394, filed on Mar. 25, 2010.

(51) Int. Cl.
*A61B 17/10* (2006.01)
*A61B 17/072* (2006.01)

(52) U.S. Cl.
CPC ..... *A61B 17/072* (2013.01); *A61B 2017/07214* (2013.01); *A61B 2017/07264* (2013.01)
USPC ........................................................ 227/177.1

(58) Field of Classification Search
CPC ............... A61B 17/072; A61B 17/068; A61B 2017/07214; A61B 2017/2946; A61B 2017/07264; A61B 2017/07257; A61B 2017/07271
USPC ...................... 227/175.1–182.1, 19
See application file for complete search history.

(56) References Cited

U.S. PATENT DOCUMENTS

| | | | |
|---|---|---|---|
| 2,891,250 A | 6/1959 | Fagge | |
| 3,080,564 A | 3/1963 | Strekopitov et al. | |
| 3,252,643 A | 5/1966 | Strekopitov et al. | |
| 3,269,630 A | 8/1966 | Fleischer | |
| 3,275,211 A | 9/1966 | Hirsch et al. | |
| 3,315,863 A | 4/1967 | O'Dea | |
| 3,494,533 A * | 2/1970 | Green et al. | 227/19 |
| 3,589,589 A | 6/1971 | Akopov | |
| 3,692,224 A | 9/1972 | Astafiev et al. | |
| 3,795,034 A | 3/1974 | Strekopytov et al. | |
| 3,822,818 A | 7/1974 | Strekopytov et al. | |
| 3,935,981 A | 2/1976 | Akopov et al. | |
| 3,949,923 A | 4/1976 | Akopov et al. | |
| 4,047,654 A | 9/1977 | Alvarado | |
| 4,216,891 A | 8/1980 | Behlke | |
| 4,244,372 A | 1/1981 | Kapitanov et al. | |
| 4,272,002 A * | 6/1981 | Moshofsky | 227/19 |
| 4,273,281 A * | 6/1981 | Smith et al. | 227/152 |
| 4,296,881 A | 10/1981 | Lee | |
| 4,305,539 A | 12/1981 | Korolkov et al. | |
| 4,354,628 A | 10/1982 | Green | |
| 4,378,901 A | 4/1983 | Akopov et al. | |
| 4,383,634 A | 5/1983 | Green | |
| 4,402,444 A | 9/1983 | Green | |
| 4,415,112 A | 11/1983 | Green | |
| D273,513 S | 4/1984 | Spreckelmeier | |
| 4,442,964 A | 4/1984 | Becht | |
| 4,470,533 A | 9/1984 | Schuler | |
| 4,475,679 A | 10/1984 | Fleury, Jr. | |
| 4,485,811 A | 12/1984 | Chernousov et al. | |

(Continued)

*Primary Examiner* — Andrew M Tecco

(57) ABSTRACT

An alignment pin assembly for a surgical stapler includes an alignment pin configured to be advanced prior to actuation of a stapler and an end cap defining an opening configured to receive the alignment pin prior to actuation of the stapler. The end cap includes an alignment pin contact area formed about the opening configured to direct the alignment pin into the opening.

19 Claims, 6 Drawing Sheets

(56) References Cited

U.S. PATENT DOCUMENTS

| | | |
|---|---|---|
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A * | 3/1986 | Green et al. ............... 227/19 |
| 4,580,712 A * | 4/1986 | Green ............... 227/19 |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | DiGiovanni et al. |
| 4,606,344 A | 8/1986 | DiGiovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A * | 12/1991 | Rodak et al. ............... 227/175.2 |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A * | 6/1993 | Bilotti et al. ............... 227/175.1 |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A * | 3/1998 | Clark et al. ............... 227/175.1 |
| 5,735,445 A | 4/1998 | Vidal et al. |
| 5,772,099 A * | 6/1998 | Gravener ............... 227/176.1 |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 8,353,436 B2 * | 1/2013 | Kasvikis ............... 227/175.1 |
| 2004/0084505 A1 | 5/2004 | Bilotti et al. |
| 2004/0164123 A1 | 8/2004 | Racenet et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2006/0201992 A1 | 9/2006 | Racenet et al. |
| 2006/0273135 A1 | 12/2006 | Beetel et al. |
| 2007/0029364 A1 | 2/2007 | Kruszynski et al. |
| 2007/0039996 A1 | 2/2007 | Mather et al. |
| 2007/0039997 A1 | 2/2007 | Mather et al. |
| 2007/0095877 A1 | 5/2007 | Racenet et al. |
| 2007/0187456 A1 | 8/2007 | Viola et al. |
| 2007/0221702 A1 | 9/2007 | Kruszynski |
| 2007/0262116 A1 * | 11/2007 | Hueil et al. ............... 227/175.1 |
| 2008/0023523 A1 | 1/2008 | Racenet et al. |
| 2008/0093415 A1 | 4/2008 | Bilotti |
| 2009/0255976 A1 | 10/2009 | Marczyk et al. |
| 2009/0261143 A1 | 10/2009 | Wixey et al. |
| 2009/0277948 A1 | 11/2009 | Beardsley et al. |
| 2009/0302092 A1 | 12/2009 | Kasvikis et al. |
| 2009/0302093 A1 | 12/2009 | Kasvikis |
| 2010/0038403 A1 | 2/2010 | D'Arcangelo |
| 2010/0048988 A1 | 2/2010 | Pastorelli et al. |
| 2010/0200637 A1 | 8/2010 | Beetel |
| 2010/0243705 A1 | 9/2010 | Wixey et al. |
| 2010/0282818 A1 | 11/2010 | Racenet et al. |
| 2010/0282820 A1 | 11/2010 | Kasvikis |
| 2011/0042443 A1 | 2/2011 | Milliman et al. |
| 2011/0155783 A1 * | 6/2011 | Rajappa et al. ............... 227/176.1 |

* cited by examiner

PIN ALIGNMENT ASSEMBLY FOR SURGICAL STAPLER

This application claims priority from provisional application Ser. No. 61/317,394, filed Mar. 25, 2010, the entire contents of which are incorporated herein by reference.

BACKGROUND

1. Technical Field

The present disclosure relates generally to a surgical stapling apparatus and, more specifically, to a surgical stapling apparatus having a pin alignment assembly including lead-in and/or catch features.

2. Background of Related Art

Surgical stapling instruments used for applying parallel rows of staples through compressed living tissue are well known in the art, and are commonly used, for example, for closure of tissue or organs prior to trans-section, prior to resection, or in anastomoses, and for occlusion of organs in thoracic and abdominal procedures.

Typically, such surgical stapling instruments include an anvil assembly, a cartridge assembly for supporting an array of surgical staples, an approximation mechanism for approximating the anvil and cartridge assemblies, an alignment pin assembly for capturing tissue between the cartridge and anvil assemblies and for maintaining alignment between the cartridge and anvil assemblies during approximation and firing, and a firing mechanism for ejecting the surgical staples from the cartridge assembly. The approximation mechanism and the firing mechanism can include distinct actuators for effecting approximation and firing of the staples. An alignment pin assembly advances an alignment pin from the cartridge assembly into engagement with the anvil. The alignment pin assembly can be automatically actuated upon operation of the approximation mechanism and/or manually operated.

Typically, the distal end of the alignment pin is received within an opening formed in the anvil assembly. The opening formed in the anvil assembly is typically sized slightly larger in diameter than the diameter of the alignment pin being received therein. This configuration prevents lateral movement of the alignment pin prior to and during firing of the surgical staples.

It would be advantageous to provide an improved alignment pin assembly to expand manufacturing tolerances and accommodate for misalignment.

SUMMARY

In one aspect of the present disclosure, an alignment pin assembly is provided including an alignment pin configured to be advanced prior to actuation of a stapler and an end cap defining an opening configured to receive the alignment pin prior to actuation of the stapler. The end cap includes an alignment pin contact area formed about the opening configured to direct the alignment pin into the opening.

The alignment pin contact area may define a substantially V-shaped or U-shaped profile. In some embodiments, the contact area can have curved surfaces. The alignment pin contact area may define in one embodiment an angle of about one-hundred fifty degrees to about one-hundred seventy degrees, and preferably in one embodiment an angle of about one-hundred sixty degrees. The end cap may be configured for reception on a distal end of an anvil assembly. Alternatively, the end cap may be integrally formed with an anvil assembly.

In one embodiment, the end cap may include a boss feature on a distal side of the opening for frictionally engaging the alignment pin. The boss feature can include at least a first and second boss member. Each of the boss members may include an alignment pin engagement surface.

Also provided in another aspect is a surgical stapler including a handle assembly, an elongated body extending from the handle assembly, a cartridge assembly mounted on the distal end of the elongated body and including an alignment pin configured for advancement from the cartridge assembly, and an anvil assembly positioned distal of the cartridge assembly. The anvil assembly includes an opening configured to receive the alignment pin, the opening including an angled alignment pin contacting area to provide a lead in configuration.

In one embodiment, the alignment pin contact area defines a substantially V-shaped profile, while in another embodiment the alignment pin contact area defines a substantially U-shaped profile. The alignment pin contact area can define curved surfaces. The alignment pin contact area may define an angle of about one-hundred fifty degrees to about one-hundred seventy degrees, and preferably in one embodiment may define an angle of about one-hundred sixty degrees. The end cap may include a boss feature for frictionally engaging the alignment pin. The boss feature may include at least a first and second boss member. Each of the boss members may include an alignment pin engagement surface. The surgical stapler can have in some embodiments a tolerance equal to approximately half the width of the contact area, thereby enabling the alignment pin to be directed within the opening if a lateral misalignment from the opening is less than or equal to a distance measuring up to approximately half the width of the contact area.

BRIEF DESCRIPTION OF THE DRAWINGS

Embodiments of the presently disclosed surgical stapling apparatus are described herein with reference to the drawings, wherein.

DETAILED DESCRIPTION

Figure 1:
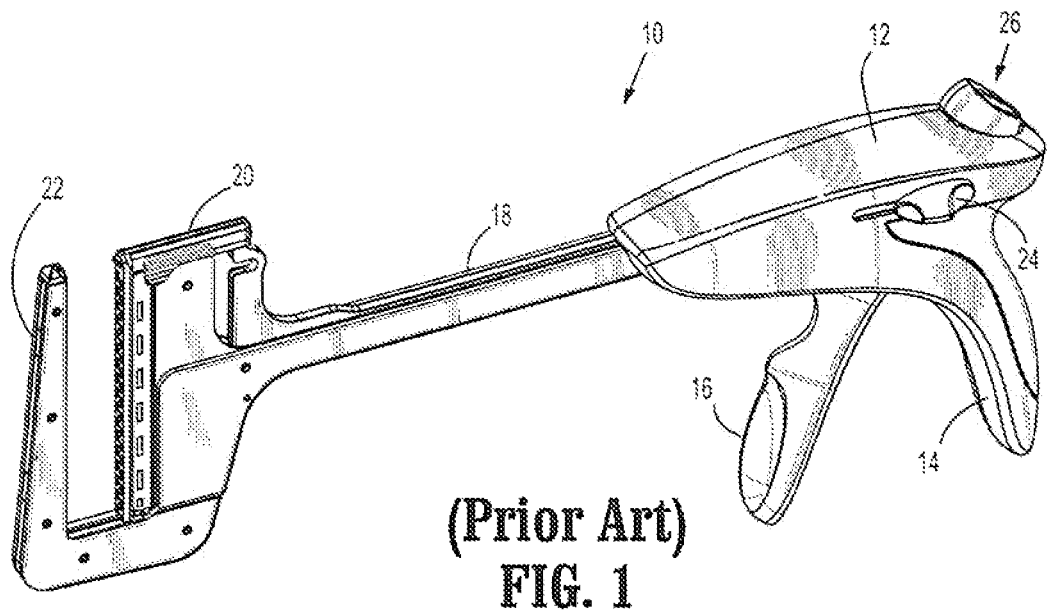
FIG. 1 is a perspective view of a prior art surgical stapling device.

Embodiments of the presently disclosed alignment pin assembly will now be described in detail with reference to the drawings, wherein like reference numerals designate corresponding elements in each of the several views. Throughout this description, the term "proximal" will refer to the portion of the instrument closer to the operator and the term "distal" will refer to the portion of the instrument further from the operator.

Figure 2:
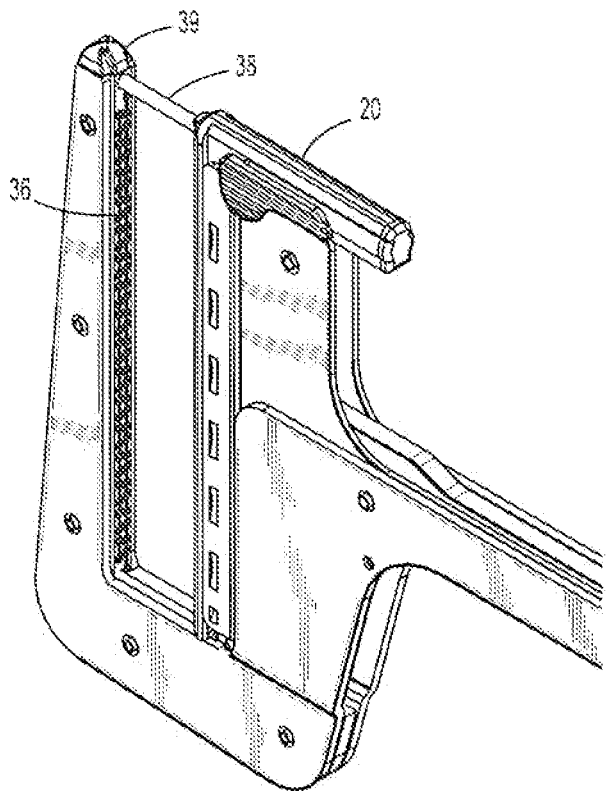
FIG. 2 is an enlarged perspective view of the distal end of the prior art surgical stapling device of FIG. 1.
Figure 3:
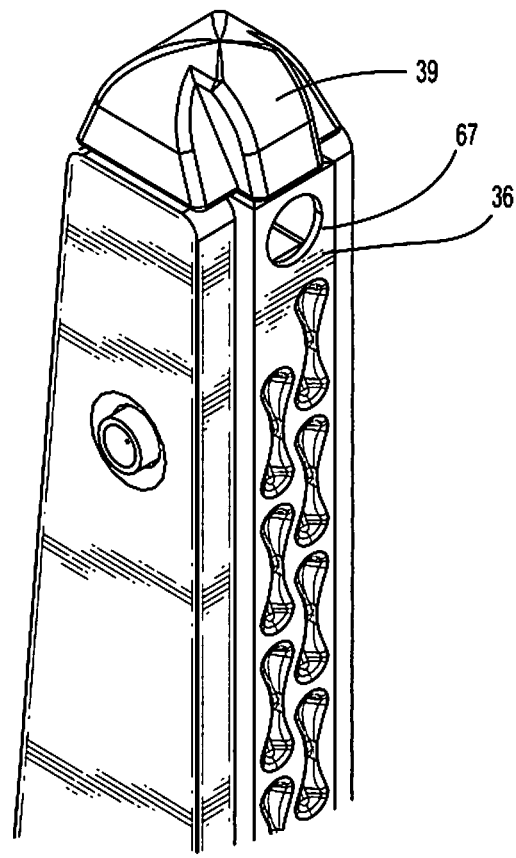
FIG. 3 is an enlarged perspective view of a portion of the anvil assembly of the prior art surgical stapling device of FIG. 1.

A prior art surgical stapling device 10 is shown in FIGS. 1-3. Briefly, stapling device 10 includes a stationary handle 14, a pivotable trigger 16, an elongated central body portion 18, a cartridge assembly 20 and an anvil assembly 22. Thumb buttons 24 are slidably positioned on each side of body 12 and are movable to manually advance an alignment pin 38 distally from cartridge assembly 20. (The pin 38 can alternately be automatically advanced upon actuation of trigger 16.) A release button 26 is positioned on the proximal portion of body 12 and is depressible to allow cartridge assembly 20 to return from an approximated position disposed adjacent to anvil assembly 22 to a position spaced from anvil assembly 22.

With particular reference to FIGS. 2 and 3, anvil assembly 22 includes an anvil 36. Anvil 36 includes an opening 67 configured to receive alignment pin 38 therethrough during operation of stapling device 10. Anvil assembly 22 further includes a cap 39. Cap 39 provides anvil assembly 22 with a smooth surface which is less likely to snag tissue during use.

Figure 4:
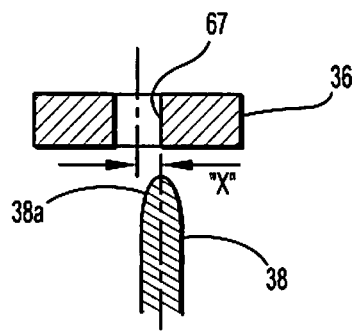
FIG. 4 is a cross-sectional schematic view of the anvil assembly and alignment pin of the prior art surgical stapling device of FIG. 1.

Turning now to FIG. 4, opening 67 formed in anvil 36 includes a diameter slightly larger than the diameter of alignment pin 38. Alignment pin 38 may include a tapered or rounded distal free end 38a. As depicted in FIG. 4, the size and configuration of alignment pin 38 and opening 67 provides surgical stapling device 10 with a tolerance equal to approximately half of the width of alignment pin 38, or a distance "x". In this manner, alignment pin 38 may be laterally misaligned a distance of "x" before distal end 38a of alignment pin 38 will not be received within opening 67. In one embodiment, "x" is equal to about 0.039 inches.

The structure and function of surgical stapler 10 has been described to the extent necessary to disclose the aspects of the present disclosure. A more detailed discussion of the structure and function of a surgical stapler that is substantially similar to surgical stapler 10 is disclosed in commonly owned U.S. Pat. No. 6,817,508 (the '508 patent), the entire contents of which are incorporated by reference herein. Although described with reference to surgical stapling device 10, the aspects of present disclosure may be modified for use with other stapling devices having an advanceable alignment pin.

Figure 6:
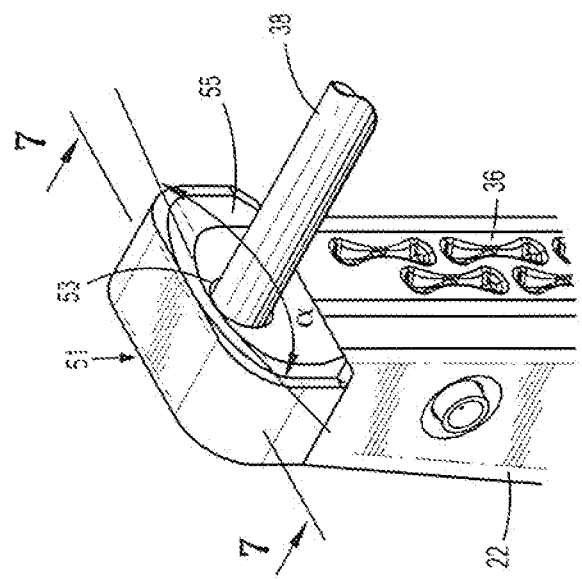
FIG. 6 is an enlarged perspective view of detail 6 of FIG. 5.
Figure 5:
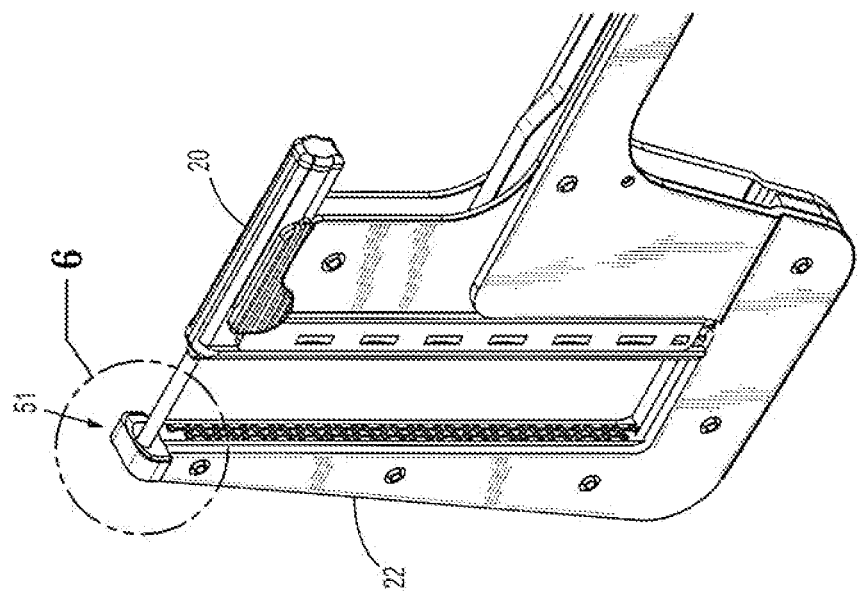
FIG. 5 is an enlarged perspective view of the distal end of the surgical stapling device of FIG. 1 including an end cap according to an embodiment of the present disclosure.
Figure 7:
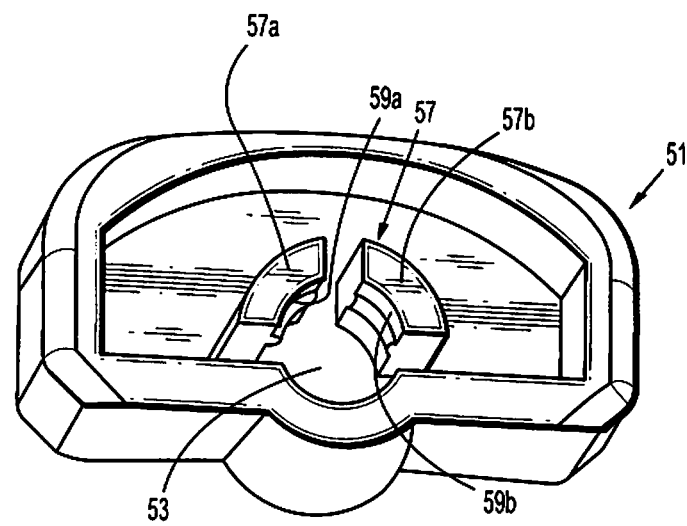
FIG. 7 is a cross-sectional end view taken along line 7-7 of FIG. 6

With reference now to FIGS. 5-7, an embodiment of an end cap according to the present disclosure is shown generally as end cap 51. End cap 51 may be composed of plastic, polymer or any other suitable material. End cap 51 defines a substantially D-shaped member configured to be received over an end of anvil assembly 22. End cap 51 may be frictionally secured to anvil assembly 22 or may instead be secured thereto using adhesives, mechanical fasteners or the like. It could also have a snap in feature or interlocking structure to engage an upper or side surface of the anvil assembly and optionally glued for additional holding. In some embodiments, end cap 51 is integrally (monolithically) formed with anvil assembly 22. As shown, end cap 51 is configured to be received on a pre-existing stapler; however, it is also envisioned that surgical staplers may be modified to incorporate the end cap. It is envisioned that the aspects of the present disclosure may be modified for use with any instrument including an alignment pin. As shown, end cap 51 is positioned above (in the orientation of FIG. 6) the rows of staple forming anvil depressions.

Figure 8:
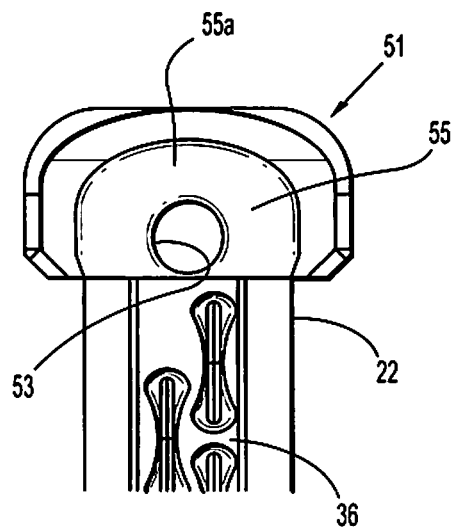
FIG. 8 is an enlarged end view of detail 6 of FIG. 5 with the alignment pin in the retracted position and not shown.
Figure 9:
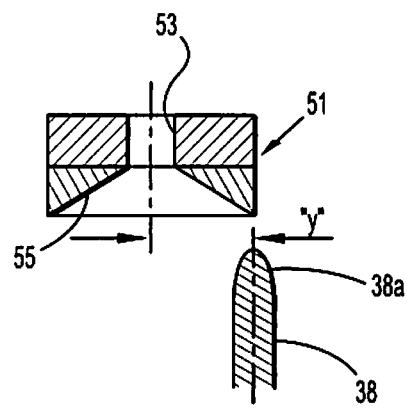
FIG. 9 is a cross-sectional view of the end cap and alignment pin of FIG. 5 prior to engagement of the alignment pin with the end cap.
Figure 10:
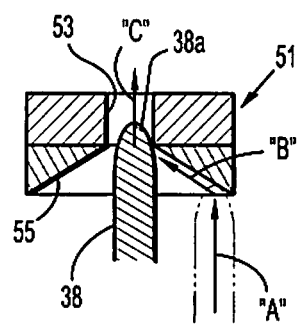
FIG. 10 is a cross-sectional view of the end cap and alignment pin of FIG. 5 upon engagement of the alignment pin with the end cap.

With reference to FIGS. 8-10, end cap 51 defines an opening 53 configured to align with an opening formed in anvil 36 of stapler 10 when end cap 51 is securely received on anvil assembly 22. End cap 51 defines an alignment pin contact area 55 about opening 53 which provides a lead in feature. Alignment pin contact area 55 is configured to direct alignment pin 38 towards opening 53. The width of alignment pin contact area 55 is limited only by the width of end cap 51. Alignment pin contact area 55 in the illustrated embodiment includes a substantially V-shaped profile defining an angle α, ranging in one embodiment by way of example from about one-hundred fifty degrees)(150°) to about one-hundred seventy degrees) (170°), and preferably, in one embodiment, about one-hundred sixty degrees)(160°). In an alternate embodiment, alignment pin contact area 55 includes a substantially U-shaped profile. An upper portion 55a of alignment pin contact area 55 also includes a curved or angled profile. Upper portion 55a of alignment pin contact area 55 is configured to further direct distal end 38a of alignment pin 38 towards opening 53 in end cap 51. In one embodiment, alignment pin contact area 55 includes a coating, e.g., silicone, configured to reduce the friction between distal end 38a of alignment pin 38 and end cap 51 to facilitate sliding of alignment pin 38 against alignment pin contact area 55.

With particular reference now to FIG. 7, the alignment pin catch feature is illustrated. End cap 51 includes a boss feature 57 configured for frictionally engaging and retaining alignment pin 38 upon receipt of distal end 38a of alignment pin 38 through opening 53. Boss feature 57 is configured to prevent premature retraction of alignment pin 38 during the actuation of stapler 10 by the interference fit provided by the ridges 59a, 59b. Boss feature 57 includes first and second boss members 57a, 57b extending inwardly about opening 53. Although shown including two boss members 57a, 57b, it is envisioned that end cap 51 may include one or more than two boss members. First and second boss members 57a, 57b each include a pin engagement surface 59a, 59b, respectively, configured to engage alignment pin 38 as distal end 38a of alignment pin 38 is received through opening 53. Pin engagement surfaces 59a, 59b may include a ridge, as shown, or may be otherwise configured to frictionally engage distal end 38a of alignment pin 38. Pin engagement surfaces 59a, 59b may include a coating, i.e., rubber (not shown), for more securely engaging alignment pin 38.

The operation of alignment end cap 51 will be described with particular reference to FIGS. 9 and 10. As noted above, alignment pin 38 may be advanced manually using thumb buttons such as button 24 of FIG. 1. Alternatively, alignment pin 38 is automatically advanced during actuation of the device such as surgical stapling device 10 of FIG. 1. Advancement of alignment pin 38, in the direction indicated by arrow "A", directs the distal end 38a of alignment pin 38 toward opening 53 of end cap 51. However, during advancement of alignment pin 38, if alignment pin 38 is out of alignment with opening 53 of cap 51, it will contact pin contact area 55. Engagement of distal end 38a of alignment pin 38 with alignment pin contact area 55 causes the directing of alignment pin 38 towards opening 53 of end cap 51, in the direction indicated by arrow "B". Upon complete advancement of alignment pin 38, in the direction indicated by arrow "C", distal end 38a of alignment pin 38 is received within opening 53 of end cap 51.

As depicted in FIGS. 9 and 10, the size and configuration of alignment pin 38 and end cap 51 provides surgical stapling device 10 with a tolerance equal to approximately half of the width of alignment pin contact area 55, or a distance "y". In this manner, alignment pin 38 may be laterally misaligned from opening 53 a distance of "y" before distal end 38a of alignment pin 38 will not be directed within opening 53. In one embodiment, "y" is equal to about 0.157 inches.

Each of pin engagement surfaces 59a, 59b, of respective first and second boss members 57a, 57b of boss feature 57 engage distal end 38a of alignment pin 38 as alignment pin 38 is received through opening 53. In this manner, boss feature 57 frictionally retains alignment pin 38 in the advanced position, thereby preventing premature retraction of alignment pin 38. Application of a sufficient proximal force will enable release from boss feature 57.

Figure 12:
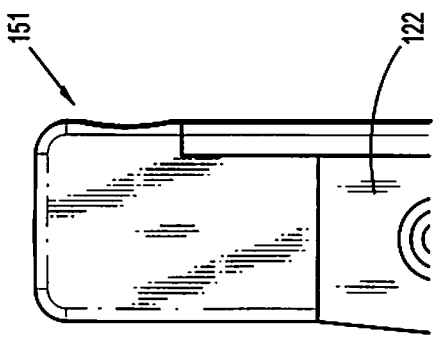
FIG. 12 is an enlarged side view of the distal end of the anvil assembly of FIG. 11.
Figure 11:
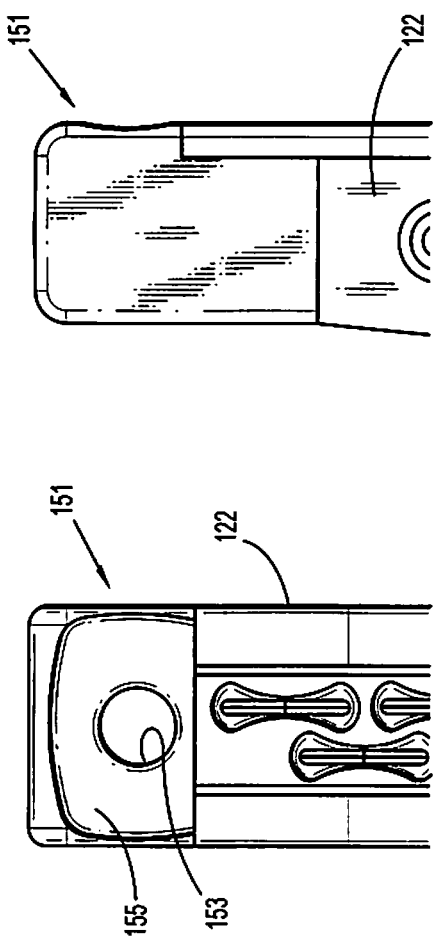
FIG. 11 is an enlarged end view of a distal end of an anvil assembly including an alternative embodiment of an end cap according to the present disclosure.
Figure 13:
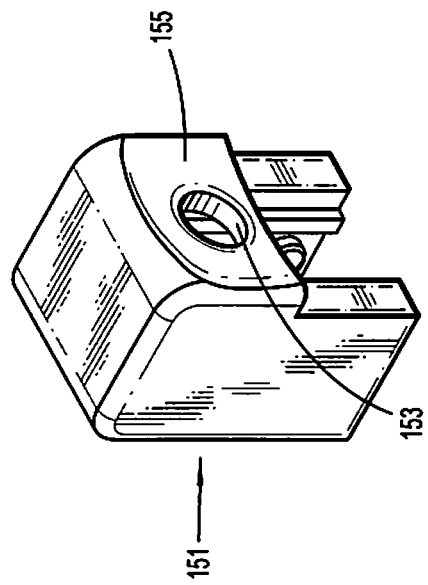
FIG. 13 is an enlarged perspective view of the end cap of FIG. 11.

With reference now to FIGS. 11-13, an alternate embodiment of an end cap according to the present disclosure is shown generally as end cap 151. End cap 151 is substantially similar to end cap 51, described hereinabove, and will therefore only be described as relates to the differences therebetween. End cap 151 is configured for secure engagement with an anvil assembly 122. End cap 151 has a spherical alignment pin contact area 155 with the curved surfaces directing the alignment pin 38 of FIGS. 8-9 toward opening 153. End cap 151 may be frictionally received on anvil assembly 122 or may instead be mechanically fastened, adhered, welded or otherwise secured thereto. End cap can alternatively be monolithically (integrally) formed with the anvil assembly. In use, alignment pin contact area 155 directs an alignment pin (not shown) into opening 153 formed therein if the alignment pin is misaligned and contacts the contact area 155 in a similar manner as contact area 55. End cap 151 may include a boss feature (not shown) as in the embodiment of FIG. 7.

It will be understood that various modifications may be made to the embodiments disclosed herein. For example, the components of the alignment pin assembly may be modified for use with other instruments including an alignment pin. Therefore, the above description should not be construed as limiting, but merely as exemplifications of preferred embodiments. Those skilled in the art will envision other modifications within the scope and spirit of the claims appended hereto.

What is claim is:

1. An alignment pin assembly for a surgical stapler comprising:
   an alignment pin movable to an advanced position; and
   an end cap defining an opening positioned and configured to receive the alignment pin, wherein the end cap includes an alignment pin contact area formed about the opening and a boss feature extending distally from a distal facing surface of the end cap, the boss feature being positioned to frictionally engage the alignment pin with an interference fit when the alignment pin is in the advanced position to frictionally retain the alignment pin in the advanced position, the alignment pin contact area being positioned and configured to direct the alignment pin into the opening.

2. The alignment pin assembly of claim 1, wherein the alignment pin contact area defines a substantially V-shaped profile.

3. The alignment pin assembly of claim 1, wherein the alignment pin contact area defines curved surfaces.

4. The alignment pin assembly of claim 1, wherein the alignment pin contact area defines an angle of one-hundred fifty degrees to one-hundred seventy degrees.

5. The alignment pin assembly of claim 1, wherein the end cap is configured to be mounted to an anvil assembly.

6. The alignment pin assembly of claim 1, wherein the alignment pin is manually advanceable.

7. The alignment pin assembly of claim 1, wherein the end cap is integrally formed with an anvil assembly.

8. The alignment pin assembly of claim 1, wherein the boss feature includes at least a first boss member and a second boss member and each of the boss members includes an alignment pin engagement surface.

9. A surgical stapler comprising:
   a handle assembly;
   an elongated body extending from the handle assembly;
   a cartridge assembly mounted on a distal end of the elongated body and including an alignment pin, the alignment pin being configured for advancement from the cartridge assembly; and
   an anvil assembly positioned distal of the cartridge assembly including an anvil defining an opening between a first surface of the anvil and a second surface of the anvil, the opening being configured to receive the alignment pin, the first surface including an alignment pin contact area positioned and configured to direct the alignment pin into the opening and the second surface including a distally extending retaining feature positioned to frictionally engage and frictionally retain the alignment pin with an interference fit when the alignment pin is advanced from the cartridge assembly.

10. The surgical stapler of claim 9, wherein the alignment pin contact area defines a substantially V-shaped profile.

11. The surgical stapler of claim 10, wherein the alignment pin contact area is angled.

12. The surgical stapler of claim 9, wherein the alignment pin contact area defines a curved profile.

13. The surgical stapler of claim 9, wherein the alignment pin contact area defines an angle of one-hundred fifty degrees to one-hundred seventy degrees.

14. The surgical stapler of claim 9, wherein the retaining feature includes at least one boss member.

15. The surgical stapler of claim 14, wherein the at least one boss member includes ridges.

16. The surgical stapler of claim 9, wherein the opening is formed on an end cap of the anvil.

17. The surgical stapler of claim 9, wherein the opening is spaced from anvil depressions of the anvil assembly.

18. The surgical stapler of claim 16, wherein the alignment pin contact area has a width and the surgical stapler has a tolerance equal to approximately half the width, thereby enabling the alignment pin to be directed within the opening if a lateral misalignment from the opening is less than or equal to a distance measuring up to approximately half the width of the alignment pin contact area.

19. An alignment pin assembly for a surgical stapler comprising:
   an alignment pin movable to an advanced position; and
   an end cap defining an opening between an outer face of the end cap and an inner face of the end cap, the opening positioned and configured to receive the alignment pin, wherein the end cap includes a boss feature positioned to frictionally engage and frictionally retain the alignment pin with an interference fit when the alignment pin is moved to the advanced position, the boss feature extending distally from the inner face of the end cap.

* * * * *